US011604195B2

(12) United States Patent
Iannotti (10) Patent No.: US 11,604,195 B2
(45) Date of Patent: Mar. 14, 2023

(54) HIGH THROUGHPUT ANALYSIS AND SORTING, AND SAMPLING INTERFACE AND ASSEMBLY FOR HIGH THROUGHPUT ANALYSIS AND SORTING (71) Applicant: Michael Iannotti, Washington, DC (US)

(72) Inventor: Michael Iannotti, Washington, DC (US)

( * ) Notice: Subject to any disclaimer, the term of this patent is extended or adjusted under 35 U.S.C. 154(b) by 0 days.

(21) Appl. No.: 17/635,729

(22) PCT Filed: Aug. 14, 2020

(86) PCT No.: PCT/US2020/070413
§ 371 (c)(1),
(2) Date: Feb. 16, 2022

(87) PCT Pub. No.: WO2021/035244
PCT Pub. Date: Feb. 25, 2021

(65) Prior Publication Data
US 2022/0268778 A1 Aug. 25, 2022

Related U.S. Application Data (60) Provisional application No. 62/890,142, filed on Aug. 22, 2019.

(51) Int. Cl.
*G01N 33/574* (2006.01)
*B01L 3/00* (2006.01)
(Continued)

(52) U.S. Cl.
CPC ...... *G01N 33/57492* (2013.01); *B01L 3/5085* (2013.01); *G01N 15/1404* (2013.01);
(Continued)

(58) Field of Classification Search
None
See application file for complete search history.

(56) References Cited

U.S. PATENT DOCUMENTS 5,094,818 A 3/1992 Longman et al.
6,315,952 B1 11/2001 Sklar et al.
(Continued)

FOREIGN PATENT DOCUMENTS

DE 9110519 U1 12/1991
EP 2725359 5/2015
(Continued)

OTHER PUBLICATIONS

Basu et al., "Purification of Specific Cell Population by Fluorescence Activated Cell Sorting (FACS)," Journal of Visualized Experiments, vol. 41, e1546, Jul. 2010. (Year: 2010).*
(Continued)

*Primary Examiner* — Matthew D Krcha
(74) *Attorney, Agent, or Firm* — Grüneberg and Myers, PLLC (57) ABSTRACT A method of analyzing and/or sorting selected cells or other biological components, for example for cell-based therapy, includes sampling a sample with an open end of a probe to obtain a fluid stream with the sample in it. The probe with the open end also has a fluid supply to convey fluid to the open end, and a fluid exhaust to convey the fluid stream away from the open end. The method then includes conveying the fluid stream to a flow cytometer and analyzing the fluid stream by flow cytometry; and/or separating it into at least two components. An apparatus with the probe connected to the flow cytometer may support this method. The method can provide for sampling of multiple samples efficiently, in particular to select cells for cell-based therapies.

20 Claims, 4 Drawing Sheets (51) Int. Cl.
  *G01N 15/14*  (2006.01)
  *G01N 35/10*  (2006.01)
  *G01N 15/00*  (2006.01)
  *G01N 15/10*  (2006.01)

(52) U.S. Cl.
  CPC ..... *G01N 15/1459* (2013.01); *G01N 35/1095* (2013.01); *B01L 2200/026* (2013.01); *B01L 2300/0832* (2013.01); *G01N 2015/0053* (2013.01); *G01N 2015/1006* (2013.01); *G01N 2015/149* (2013.01)

(56) References Cited

U.S. PATENT DOCUMENTS

| | | | |
|---|---|---|---|
| 6,506,609 B1* | 1/2003 | Wada | B01J 19/0093 422/50 |
| 6,878,556 B2* | 4/2005 | Sklar | G01N 21/6428 422/50 |
| 7,713,752 B2 | 5/2010 | Sullivan et al. | |
| 8,727,132 B2 | 5/2014 | Miltenyi et al. | |
| 9,632,066 B2 | 4/2017 | Van Berkel | |
| 9,885,032 B2 | 2/2018 | Dose et al. | |
| 10,053,665 B2 | 8/2018 | Zhang et al. | |
| 10,060,838 B2 | 8/2018 | Kertesz et al. | |
| 10,073,079 B2 | 9/2018 | Kelley et al. | |
| 10,103,015 B2 | 10/2018 | Arnold et al. | |
| 10,197,561 B2 | 2/2019 | Dose et al. | |
| 10,240,186 B2 | 3/2019 | Ionescu-Zanetti et al. | |
| 2005/0123450 A1* | 6/2005 | Gilbert | B01F 33/3017 422/81 |
| 2012/0080592 A1 | 4/2012 | Wiseman et al. | |
| 2013/0164740 A1 | 6/2013 | Wu et al. | |
| 2016/0167061 A1 | 6/2016 | McNaughton et al. | |
| 2016/0299109 A1* | 10/2016 | Van Berkel | A61B 5/443 |
| 2017/0268037 A1 | 9/2017 | Ionescu-Zanetti et al. | |
| 2017/0284922 A1 | 10/2017 | Mermod et al. | |
| 2018/0156711 A1* | 6/2018 | Vrane | G01N 15/1459 |
| 2018/0164296 A1 | 6/2018 | Pankratz et al. | |

FOREIGN PATENT DOCUMENTS

| | | |
|---|---|---|
| WO | 2019/079851 | 5/2019 |
| WO | 2020/010471 | 1/2020 |

OTHER PUBLICATIONS

Ping et al., "T-cell receptor-engineered T cells for cancer treatment: current status and future directions," Protein Cell, vol. 9, No. 3, 2018, pp. 254-266. (Year: 2018).*

Basu et al., "Purification of Specific Cell Population by Fluorescence Activated Cell Sorting (FACS)", Journal of Visualized Experiments, vol. 41, e1546, Jul. 2010, pp. 1-4.
BD Biosciences, "Introduction to Flow Cytometry: A learning Guide", Becton, Dickinson and Company, Dec. 2002, 58 pages.
"Fluidics of a Flow Cytometer", ThermoFisher Scientific, retrieved from <https://www.thermofisher.com/us/en/home/life-science/cell-analysis-learning-center/molecular-probes-school-of-fluorescence/flow-cytometry-basics/flow-cytometry-fundamentals/fluidics-flow-cytometer.html> on Jul. 11, 2019, 7 pages.
Gómez-Ríos et al, "Open port Probe Sampling Interface for the Direct Coupling of Biocompatible Solid-Phase Microextraction to Atmospheric Pressure Ionization Mass Spectrometry", Analytical Chemistry, vol. 89, 2017, pp. 3805-3809.
International Search Report dated Oct. 21, 2020 in PCT/US2020/70413, 2 pages.
Kuckuck et al., "High Throughput Flow Cytometry", Cytometry, Wiley-Liss, Inc., vol. 44, 2001, pp. 83-90.
"Microplate Dimensions Guide", Greiner Bio-One, Jul. 2007, 20 pages.
Ping et al., "T Cell receptor-engineered T cells for cancer treatment: current status ans future directions", Protein Cell, vol. 9, No. 3, 2018, pp. 254-266.
Rohaan et al., "Adoptive transfer of tumor-infiltrating lymphocytes in melanoma: a viable treatment option", Journal for Immuno Therapy of Cancer, vol. 6, No. 102, 2018, pp. 1-6.
Rohaan et al, "Adoptive cellular therapies: the current landscape", Virchows Ach., vol. 474, 2019, pp. 449-461.
Shields IV et al., "Microfluidic Cell Sorting: A Review of the Advances in the Separation of Cells from Debulking to Rare Cell Isolation", NIH public Access, Lab chip, vol. 15, No. 5, Feb. 2015, 44 pages.
Shrestha et al., "In Situ Cell-by-Cell Imaging and Analysis of Small Cell Populations by Mass Spectrometry", Analytical Chemistry, American Chemical Society, vol. 83, 2011, pp. 2947-2955.
Sutermaster et al., "Considerations for high-yield, high-throughput cell enrichment: fluorescence versus magnetic sorting", Scientific Reports, vol. 9, No. 227, 2019, pp. 1-9.
"T-cell receptor" Wikipedia, 2007(retrieved from the internet Oct. 2, 2020), 12 pages.
"Tumor-infiltrating lymphocytes", Wikipedia, 2016 (retrieved from the internet Oct. 2, 2020), 7 pages.
Written Opinion dated Oct. 21, 2020 in PCT/US2020/70413, 6 pages.
Supplementary European Search Report dated Sep. 5, 2022, in European Application No. 20854553.3, 4 pages.
European Patent Office Communication pursuant to Article 94(3) EPC dated Sep. 16, 2022, in European Application No. 20854553.3, 5 pages.

* cited by examiner

HIGH THROUGHPUT ANALYSIS AND SORTING, AND SAMPLING INTERFACE AND ASSEMBLY FOR HIGH THROUGHPUT ANALYSIS AND SORTING

CROSS-REFERENCE TO RELATED APPLICATIONS

This application is a National Stage entry under § 371 of International Application No. PCT/US2020/070413, filed on Aug. 14, 2020, which claims the benefit of U.S. Provisional Application No. 62/890,142, filed on Aug. 22, 2019. The content of each of these applications is hereby incorporated by reference in its entirety.

BACKGROUND OF THE INVENTION

Field of the Invention

A method of analysis, separation, and/or selection of components includes sampling a sample with an open end of a probe to obtain a fluid stream with the sample in it. The probe with the open end has a fluid supply to convey fluid to the open end, and a fluid exhaust to convey the fluid stream away from the open end. The method then includes conveying the fluid stream to a flow cytometer and analyzing the fluid stream by flow cytometry, and/or separating it into at least two components. The sample can be a plurality of samples provided, for example, in the wells of one or more well plates, flasks, or other containers, such as compartmentalized containers. The sample can be a sample of cells or other biological material for use in research and therapies such as cell-based therapies, including chimeric antigen receptor T cell (CAR-T) therapy, T cell receptor therapy, tumor infiltrating lymphocyte (TIL) therapy, and stem cell/induced pluripotent stem cell (iPSC) therapy. The sample can also be a sample of research reagents such as beads, which may facilitate sorting. The sample can also be a combination of biological material and research reagents.

Discussion of Related Art

U.S. Pat. No. 6,315,952 purports to teach an apparatus for supplying multiple samples for rapid processing in flow cytometry. The apparatus requires a syringe to inject a sample into a sample loop, then requires a reciprocating valve to provide the sample from the sample loop to a flow cytometer. To attempt a throughput goal of approximately 30 samples/minute, the apparatus purports to use about 1 second of aspiration, 0.8 seconds of time delay, and 0.2 seconds for the valve to be switched. U.S. Pat. No. 6,315,952 purports to avoid the potential problem of air bubbles lodging in troublesome areas such as an analysis region of a flow cell, further noting that air bubbles can be broken up and dispersed at connector junctions, causing inaccuracies in the sample draw. U.S. Pat. No. 6,315,952 is incorporated herein by reference in its entirety. U.S. Pat. No. 6,878,556 purports to teach an apparatus for high throughput flow cytometry. The apparatus provides for separation of adjacent samples by using a separation gas, such as an air bubble, to prevent mixing of adjacent samples. As a probe, the apparatus preferably uses a stainless steel needle. U.S. Pat. No. 6,878,556 is incorporated herein by reference in its entirety.

In the field of mass spectrometry and high performance liquid chromatography, U.S. Pat. No. 9,632,066 discloses a sampling probe having an open end. In the sampling probe, a liquid supply conduit delivers liquid to the open end of the probe at a first flow rate, and a liquid exhaust removes liquid at a second flow rate lower than the first flow rate. The sample material is received into the open end of the probe. The probe is useful for mass spectrometry and high performance liquid chromatography. U.S. Pat. No. 9,632,066 does not mention applications in flow cytometry, nor does it mention avoidance of air or other gas in the liquid provided from the probe, nor does it mention sorting or selection of cells, viruses, proteins, or other biological materials or of research reagents such as beads. U.S. Pat. No. 9,632,066 is incorporated herein by reference in its entirety.

Also in the field of mass spectrometry and high performance liquid chromatography, U.S. Pat. No. 10,060,838 discloses a sampling probe having an open end. In the sampling probe, a liquid supply conduit delivers liquid to the open end of the probe at a first flow rate, and an exhaust conduit removes liquid at a second flow rate higher than the first flow rate. A gas flow containing the sample is received into the open end of the probe. The probe is useful for mass spectrometry and high performance liquid chromatography. U.S. Pat. No. 10,060,838 does not mention applications in flow cytometry, nor does it mention sorting or selection of cells, viruses, proteins, or other biological materials or of research reagents such as beads, and its method require introduction of air or another gas into the probe, thereby creating a gas/liquid interface in the exhaust conduit. U.S. Pat. No. 10,060,838 is incorporated herein by reference in its entirety.

Additionally in the field of mass spectrometry, U.S. Pat. No. 10,103,015 discloses a sampling interface which is fluidly coupled to an ion source. This interface includes a sampling probe having an outer capillary tube for providing a fluid to a distal end of the probe and an inner capillary tube for removing a fluid from a distal end of the probe. A flow rate through the outer capillary tube can be temporarily increased relative to the flow rate through the inner capillary tube such that the fluid in the distal end of the probe overflows to clean any residual sample deposited by the withdrawn substrate and/or to prevent any airborne material from being transmitted into the inner capillary tube. U.S. Pat. No. 10,103,015 does not mention applications in flow cytometry, nor does it mention avoidance of air or other gas, as such, in the fluid provided from the probe, nor does it mention sorting or selection of cells, viruses, or proteins or of research reagents such as beads. U.S. Pat. No. 10,103,015 is incorporated herein by reference in its entirety.

The above-discussed art lacks the ability to provide high sample throughput for flow cytometry or flow cytometry sorting without introducing air bubbles or using a complicated system of syringes, loops, and valves.

Shields IV, C. W. et al, "Microfluidic Cell Sorting: A Review of the Advances in the Separation of Cells from Debulking to Rare Cell Isolation" *Lab Chip* 2015 15(5): 1230-1249 informs about the state of microfluidic cell sorting devices, providing details on and alternatives to other types of flow cytometry cell sorting. It describes classification and current methods for active and passive sorting including fluorescent label-based, bead-based, and label-free sorting. It also describes the principles by which cells are being sorted for each methodology. Shields IV, C. W. et al, "Microfluidic Cell Sorting: A Review of the Advances in the Separation of Cells from Debulking to Rare Cell Isolation" *Lab Chip* 2015 15(5):1230-1249 is incorporated herein by reference in entirety.

Ping, Y. et al., "T-cell receptor-engineered T cells for cancer treatment: current status and future directions" *Protein Cell* 2018 9(3):254-256 discusses the great degree of potential in various cell-based therapy techniques for cancer treatment. It briefly mentions a high throughput investigation but does not discuss high throughput sampling or the sorting or selection of different components in one or more samples. Ping, Y. et al., "T-cell receptor-engineered T cells for cancer treatment: current status and future directions" *Protein Cell* 2018 9(3):254-256 is incorporated herein by reference in entirety. As other references regarding cell-based therapies, Rohaan, M. W., et al., "Adoptive transfer of tumor-infiltrating lymphocytes in melanoma: a viable treatment option" *Virchows Archiv* 2019 474(4): 449-461 is incorporated herein by reference in entirety, and Rohaan, M. W. et al., "Adoptive transfer of tumor-infiltrating lymphocytes in melanoma: a viable treatment option" *J. Immuno-Therapy of Cancer* 2018 6:102 is incorporated herein by reference in entirety.

Sutermaster, B. et al., "Considerations for high-yield, high-throughput cell enrichment: fluorescence versus magnetic sorting" *Scientific Reports* 2019 9:227, 1-9 notes the importance of high-throughput cell sorting for cell-based therapies, comparing the speeds of fluorescence sorting and magnetic sorting. However, it does not particularly mention the processing of large numbers of different and/or separate samples, nor does it mention problems with air or other gas bubbles in the intake of a plurality of samples to be sorted. Sutermaster, B. et al., "Considerations for high-yield, high-throughput cell enrichment: fluorescence versus magnetic sorting" *Scientific Reports* 2019 9:227, 1-9 is incorporated herein by reference in entirety.

SUMMARY OF THE INVENTION

An analysis and/or sorting method comprises conveying a fluid to an open end of a probe; collecting a sample, comprising at least two components, into the open end of a probe; removing a fluid stream comprising the sample and the fluid from the open end of the probe; conveying the fluid stream to a flow cytometer and analyzing the sample in the fluid stream by flow cytometry, and/or separating the fluid stream into at least two components. "Flow cytometry" may refer to any process involving the detection of a property or properties of a collection of cells, particles, or molecules in a fluid suspension, and measurement and/or sorting based on the property or properties, using the fluidity of the suspension. The property or properties may be related to one or more labels provided on the collection of cells, particles, or molecules, such as a fluorescent, magnetic, isotopic, or chemical label. Additionally or alternatively, the property or properties may be unrelated to any label, for example wherein the property is the size, shape, density, binding capability, conductivity, or acoustic properties of a cell, particle, or molecule. The method can reduce or avoid the presence of air or gas bubbles in a sample provided to a flow cytometer, in particular a plurality of samples provided to a flow cytometer in high throughput, with a simple probe that does not require a complicated system of syringes, loops, and valves. A "flow cytometer" may refer to any device suitable for detection of a property or properties of a collection of cells, particles, or molecules in a fluid suspension, and measurement and/or sorting based on the property or properties, using the fluidity of the suspension. A flow cytometer may detect a property or properties related to a label, such as a fluorescent, magnetic, isotopic, or chemical label. Additionally or alternatively, a flow cytometer may detect a property or properties unrelated to any label, for example wherein the property is the size, shape, density, binding capability, conductivity, or acoustic properties of a cell, particle, or molecule Examples of techniques utilizing flow cytometers include fluorescence-activated cell sorting (FACS), magnetic-activated cell sorting (MACS), and microfluidic immunomagnetic cell sorting (MICS).

An analysis and/or sorting system comprises a probe, a flow cytometer, and a connection configured to convey a fluid from the probe to the flow cytometer. The probe comprises an open end, a fluid supply configured to convey the fluid to the open end, and a fluid exhaust configured to convey the fluid stream away from the open end. The system can reduce or avoid the presence of air bubbles in a sample provided to a flow cytometer, in particular a plurality of samples provided to a flow cytometer in high throughput, with a simple probe that does not require a complicated system of syringes, loops, and valves.

A sampling method comprises conveying a fluid through a fluid supply of a probe to an open end of the probe, collecting a sample into the open end of a probe, and removing a fluid stream from the open end of the probe through a fluid exhaust of the probe, the fluid stream comprising the at least one sample and the fluid. In the sampling method, (1) the fluid is an aqueous saline solution or a cell culture medium, or (2) the fluid is water, and the method further comprises adding an aqueous saline solution to the fluid stream. The method can reduce or avoid the presence of air bubbles in a sample to be provided to a flow cytometer, in particular a plurality of samples provided to a flow cytometer in high throughput, with a simple probe that does not require a complicated system of syringes, loops, and valves. The method can also provide a consistent flow of fluid through the probe to wash the probe in between sampling without the addition of manual or automated washing steps.

A first embodiment includes an analysis and/or sorting method, comprising: conveying a first fluid within a probe to an open end of a probe; collecting at least one sample, comprising at least one first component and at least one second component, into the open end of a probe; removing a fluid stream comprising the at least one sample and the first fluid from the open end of the probe; conveying the fluid stream to a flow cytometer and analyzing the fluid stream by flow cytometry, and/or separating the fluid stream into at least a first separated stream comprising the at least one first component and a second separated stream comprising the at least one second component by flow cytometry.

A second embodiment includes the method of the first embodiment, wherein the fluid stream is substantially free of air bubbles, or wherein the fluid stream is substantially free of a gas/liquid interface, or wherein the fluid stream is substantially free of both air bubbles and a gas/liquid interface.

A third embodiment includes the method of the first and/or second embodiments, wherein the at least one sample comprises a first sample, initially contained in a first container, and a second sample, initially contained in a second container.

A fourth embodiment includes the method of the third embodiment, wherein the first container is a first well in a plate and the second container is a second well in the same plate.

A fifth embodiment includes the method of the third embodiment, wherein the first container is a well in a first plate and the second container is a well in a second plate. In a further embodiment, the at least one sample comprises a plurality of samples contained in a plurality of containers, and the plurality of containers are wells in one well plate or in a plurality of well plates. The containers can also be compartments within a compartmentalized container or array or collection of containers.

A sixth embodiment includes the method of any preceding embodiment, wherein the at least one sample comprises a plurality of samples, and wherein samples are collected at a rate of greater than 30 samples per minute, and optionally, wherein collecting the plurality of samples comprises at least partial insertion of the probe into a plurality of containers or transferring the plurality of samples into the probe.

A seventh embodiment includes the method of any preceding embodiment, wherein the first fluid is water or a sheath fluid or other fluid medium suitable for flow cytometry or flow cytometry sorting.

An eighth embodiment includes the method any preceding embodiment, wherein the first fluid is a buffered aqueous saline solution or a cell culture medium.

A ninth embodiment includes the method of the eighth embodiment, wherein the first fluid is a buffered aqueous saline solution comprising a phosphate buffer.

A tenth embodiment includes the method of any preceding embodiment, wherein the at least one sample comprises cells.

An eleventh embodiment includes the method of any preceding embodiment, wherein at least a portion of the sample is labeled, for example with a fluorescent, magnetic, isotopic, or chemical label. In other embodiments, the sample is not labeled, and analysis and/or sorting occurs based on at least one other detected property.

A twelfth embodiment includes the method of the eleventh embodiment, wherein the at least one first component comprises a labeled component and wherein the at least one second component comprises a component which is not labeled.

A thirteenth embodiment includes the method of any of the preceding embodiments, wherein the at least one sample comprises leukocytes, stem cells, or circulating tumor cells.

A fourteenth embodiment includes the method of any of the preceding embodiments, wherein the at least one sample comprises T cells.

A fifteenth embodiment includes the method of the fourteenth embodiment, wherein at least some of the T cells comprise a T cell receptor or a chimeric antigen receptor.

A sixteenth embodiment includes the method of any of the preceding embodiments, wherein the at least one sample comprises tumor infiltrating lymphocytes.

A seventeenth embodiment includes the method of any of the first through fifteenth embodiments, wherein the at least one first component comprises T cells comprising a T cell receptor or a chimeric antigen receptor and wherein the at least one second component comprises T cells which are substantially free of T cell receptors and chimeric antigen receptors.

An eighteenth embodiment includes the method of any preceding embodiment, wherein the conveying the first fluid to the open end of the probe comprises pumping the first fluid with a first pump, and wherein removing the fluid stream from the open end of the probe comprises removing the fluid stream with a second pump.

A nineteenth embodiment includes the method of the eighteenth embodiment, further comprising controlling a first flow rate of the first fluid into the open end of the probe, and simultaneously controlling a second flow rate of the fluid stream from the open end of the probe.

A twentieth embodiment includes the method of any preceding embodiment, further comprising adding a second fluid to the fluid stream, before, during, or after conveying the fluid stream to the flow cytometer, wherein the second fluid is the same as or different from the first fluid.

A twenty-first embodiment includes an analysis and/or sorting system, comprising a probe, a flow cytometer, and a connection between the probe and the flow cytometer, configured to convey a fluid from the probe to the flow cytometer, wherein the probe comprises an open end, a fluid supply configured to convey the fluid to the open end, and a fluid exhaust configured to convey the fluid stream away from the open end to the flow cytometer.

A twenty-second embodiment includes the system of the twenty-first embodiment, wherein the fluid supply and the fluid exhaust are coaxial.

A twenty-third embodiment includes the system of the twenty first and/or twenty second embodiments, wherein a width of the probe at its open end is less than 3.3 mm.

A twenty-fourth embodiment includes the system of the twenty first and/or twenty second embodiments, wherein a width of the probe at its open end is less than 1.3 mm.

A twenty-fifth embodiment includes a method of sorting at least one sample with the system of any of the twenty-first through twenty-fourth embodiments, the method comprising conveying a fluid to the open end of the probe with the fluid supply; collecting the at least one sample, comprising at least one first component and at least one second component, into the open end of a probe; removing a fluid stream comprising the at least one sample and the fluid from the open end of the probe with the fluid exhaust; conveying the fluid stream through the connection to the flow cytometer and analyzing the fluid stream by flow cytometry, and/or separating the fluid stream into at least a first separated stream comprising the at least one first component and a second separated stream comprising the at least one second component by cell sorting.

A twenty-sixth embodiment includes a sampling method, comprising conveying a fluid through a fluid supply of a probe to an open end of the probe, collecting at least one sample into the open end of a probe, and removing a fluid stream from the open end of the probe through a fluid exhaust of the probe, the fluid stream comprising the at least one sample and the fluid. In the twenty-sixth embodiment, the fluid itself may be an aqueous saline solution or a cell culture medium, or the fluid may be water, and an aqueous saline solution is further added to the fluid stream.

A twenty-seventh embodiment includes the method of the twenty-sixth embodiment, wherein the fluid is a buffered aqueous saline sheath fluid suitable for flow cytometry.

A twenty-eighth embodiment includes the method of the twenty-sixth and/or twenty-seventh embodiments, wherein the fluid stream is substantially free of air bubbles, and wherein the fluid stream is substantially free of a gas/liquid interface.

A twenty-ninth embodiment includes the method of any of the twenty-sixth through twenty-eighth embodiments, wherein the at least one sample comprises a plurality of samples, and wherein samples are collected at a rate of greater than 30 samples per minute, and optionally, wherein collecting the plurality of samples comprises at least partial insertion of the probe into a plurality of containers, or transferring the plurality of samples into the probe.

DETAILED DESCRIPTION OF THE INVENTION

Figure 1:
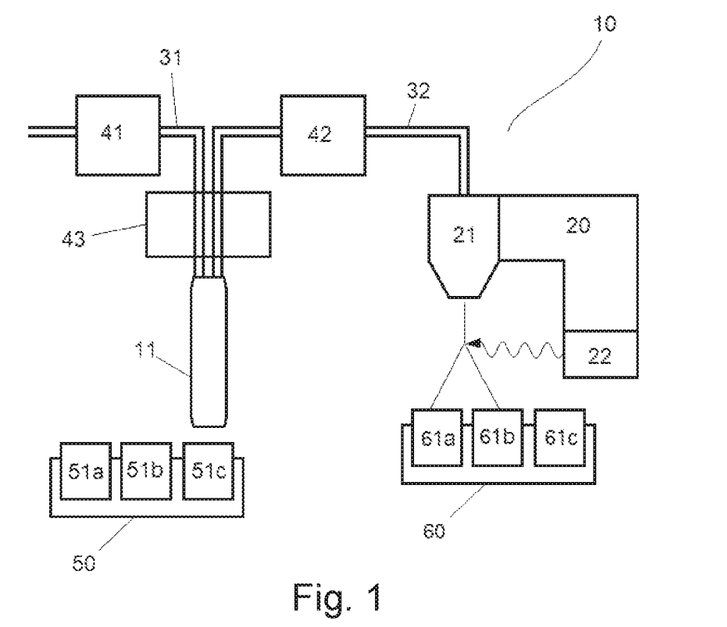
FIG. 1 shows an embodiment of a system for flow cytometry, in a state in which the probe is not collecting a sample.
Figure 2:
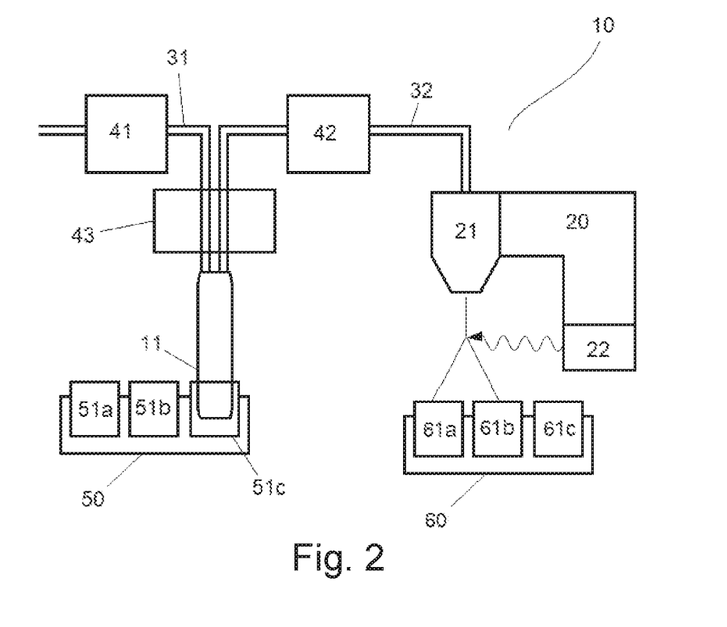
FIG. 2 shows an embodiment of a system for flow cytometry, in a state in which the probe is collecting a sample.

FIGS. 1 and 2 show an embodiment of an analysis and/or sorting system 10, shown in these figures in the presence of a well plate 50. In this embodiment, analysis and/or sorting system 10 includes probe 11, probe input line 31 configured to provide a fluid to probe 11, and probe to flow cytometer line 32 configured to remove a fluid from probe 11 and/or provide a fluid to flow cytometer 20. Also in this embodiment, probe input pump 41 is configured to move a fluid through probe input line 31 to probe 11, and probe to flow cytometer pump 42 is configured to move a fluid through probe to flow cytometer line 32, away from probe 11 and/or into flow cytometer 20. Autosampler 43 in this embodiment may be configured to move probe 11 between wells 51a, 51b, and 51c of well plate 50. In FIGS. 1 and 2, the embodiment of probe 11 is depicted in an orientation such that an open end thereof would be pointing downward during operation. However, in other embodiments, for example where the wells or other sample container or containers are sufficiently narrow so as to retain the sample by forces such as surface tension or adhesion even in other orientations, the open end of the probe may point in an upward direction, a sideways direction, or at a skew angle with respect to a vertical direction. In some such embodiments, an upward direction for the probe and an inverted orientation of the sample container or containers, wherein an open end of the sample container or containers faces downward, may be particularly preferred.

In some embodiments, analysis and/or sorting system 10 preferably orients probe 11 such that it can be directed into a sample container, such as a sample holder, tube, cartridge or microchip, and/or well plate, or compartments within a compartmentalized container or array or collection of containers. FIG. 1 shows probe 11 oriented to collect a sample from well 51c in well plate 50. FIG. 2 shows probe 11 collecting a sample from well 51c in well plate 50. In the embodiment shown in FIGS. 1 and 2, autosampler 43 is configured to reposition probe 11 for collection of samples in well 51a and well 51b in well plate 50. In other embodiments, autosampler 43 may be configured to reposition the well plate 50 for collection of samples in well 51a and well 51b by probe 11, and probe 11 may be provided in a stationary position.

Figure 3:
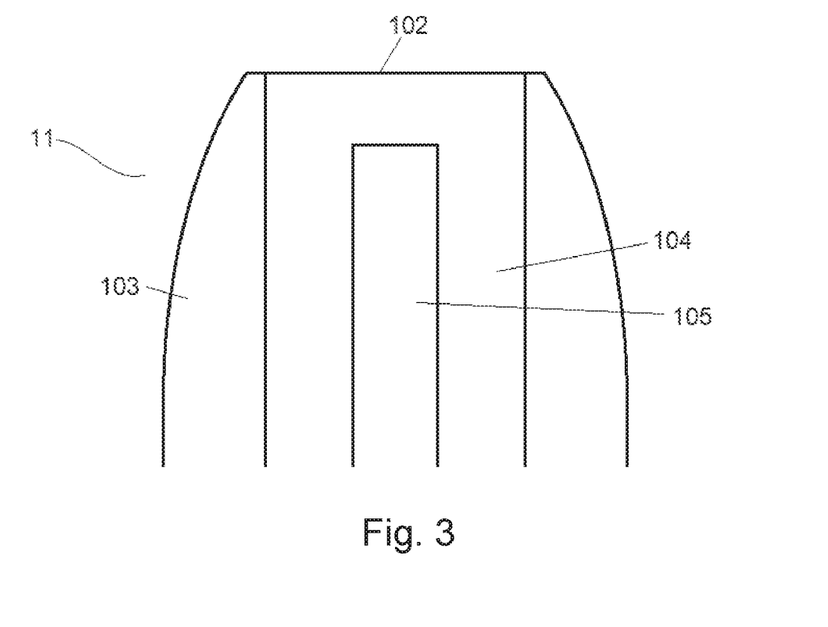
FIG. 3 is a cross-sectional view of an embodiment of a probe having an open end.
Figure 4:
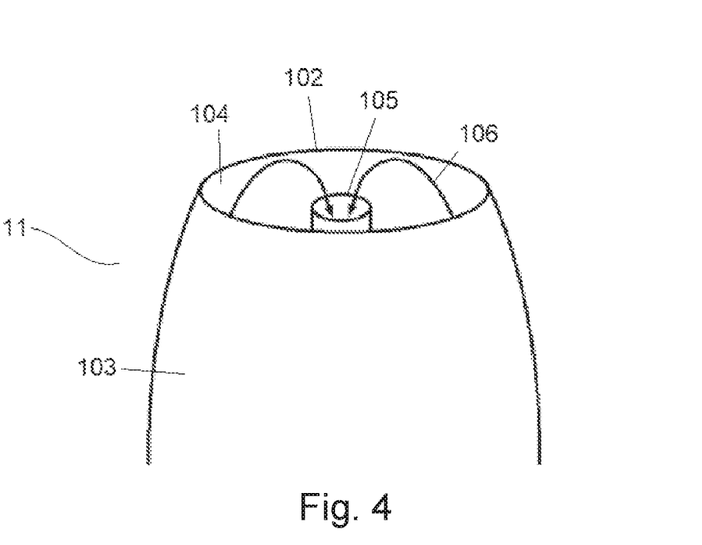
FIG. 4 is a perspective view of an embodiment of a probe having an open end.
Figure 5:
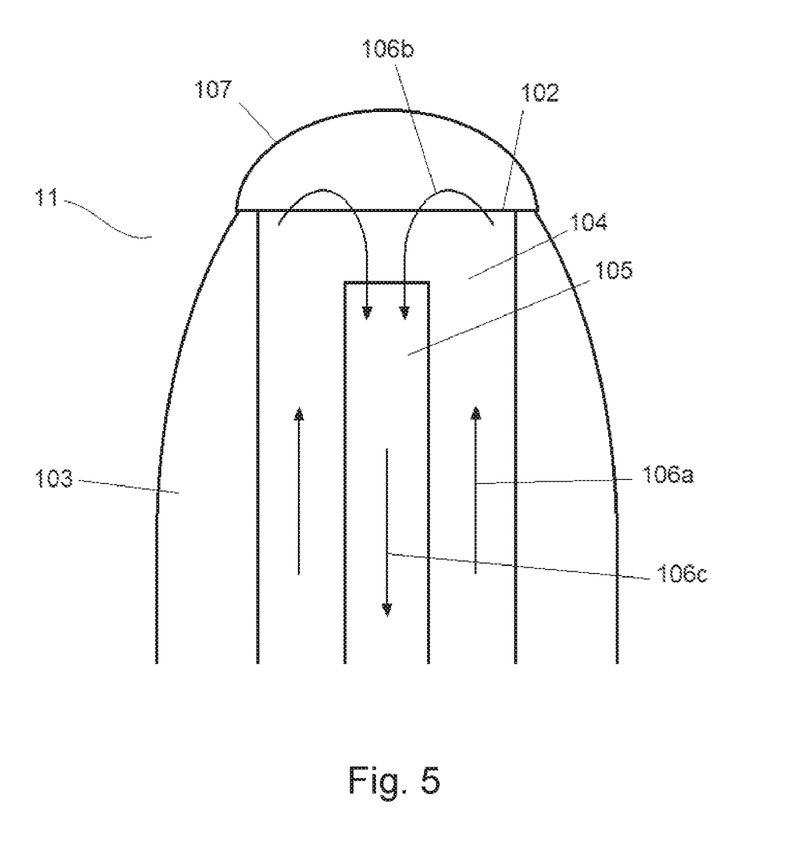
FIG. 5 is a cross-sectional view of an embodiment of a probe having an open end and in a working state.

FIGS. 3, 4, and 5 show an embodiment of a probe 11. In this embodiment, probe 11 comprises an outer wall 103, an open end 102 at an end of the outer wall 103 which in these views is pointed upward, a fluid supply 104 configured for providing fluid to the open end 102, and a fluid exhaust 105 configured for removing fluid from open end 102.

In the embodiment of probe 11 shown in FIGS. 3, 4, and 5, the fluid supply 104 is an annular region immediately within outer wall 103, and fluid exhaust 105 is a coaxial conduit positioned centrally in the probe 11. In some embodiments, an opening of fluid exhaust 105 may not extend axially for the entire length of outer wall 103 extending to open end 102, leaving some space at open end 102 for flow to more readily occur. In other embodiments, an opening of fluid exhaust 105 may extend axially for the entire length of the outer wall 103 extending to open end 102, or may extend axially even further than the entire length of the outer wall 103 and out from the open end 102.

In other embodiments, fluid supply 104 and fluid exhaust 105 can be configured differently. For example, in some other embodiments, the fluid exhaust 105 is an annular region immediately within outer wall 103, and fluid supply 104 is a coaxial conduit positioned centrally in the probe 11. In other embodiments, the fluid supply 104 may be provided as a plurality of fluid supply conduits and/or the fluid exhaust 105 may be provided as a plurality of fluid exhaust conduits. Conduits of the fluid supply 104 and/or the fluid exhaust 105 may be provided as shown in FIGS. 3, 4, and 5 in a parallel direction, or in other embodiments may be provided at oblique angles from one another.

In the aforementioned embodiment of probe 11 as shown in FIGS. 4 and 5, probe 11 is configured to provide flow of a fluid along a flow path 106. In such embodiment, fluid supply 104 can provide a fluid to open end 102 of probe 11 along incoming flow path 106a, then the fluid can flow through open end 102 along open-end flow path 106b, then the fluid can flow into outgoing flow path 106c through fluid exhaust 105. In this or other embodiments, open-end flow path 106b can include paths of flow which are less direct than as depicted in FIGS. 4 and 5, extending into open end 102 which then forms fluid dome 107. To measure or control the flow of a fluid inward through fluid supply 104, fluid supply 104 can include a flow meter and/or a flow regulator. Similarly, but independently, to measure or control the flow of a fluid outward through fluid exhaust 105, fluid exhaust 105 can include a flow meter and/or a flow regulator.

The material or materials constituting probe 11 are not particularly limited. Any of outer wall 103, fluid supply 104, and/or fluid exhaust 105 can comprise at least one metal, metal alloy, plastic, glass, ceramic, or any combination thereof, preferably comprising stainless steel and/or medical-grade plastic. Any part or entirety of outer wall 103, fluid supply 104, and/or fluid exhaust 105 can be coated or uncoated, preferably coated with a hydrophobic or hydrophilic coating. In some embodiments, at least a portion of outer wall 103, fluid supply 104, and/or fluid exhaust 105 can comprise a hydrophilic material or be provided with a hydrophilic coating, thereby providing an adhesive effect with a fluid flowing along flow path 106 and/or the fluid in fluid dome 107. In the same or other embodiments, at least a portion of outer wall 103, fluid supply 104, and/or fluid exhaust 105 can comprise a hydrophobic material or be provided with a hydrophobic coating, thereby avoiding an adhesive effect with a fluid in order to better form a desired dome shape for fluid dome 107.

In some embodiments, probe 11 can further include a fluid collection conduit, configured to collect excess or overflowing fluid from open end 102. Such a fluid collection conduit may be positioned within or provided on outer wall 103. The fluid collection conduit can comprise an opening or a plurality of openings, preferably located proximally to open end 102. The opening or openings of the fluid collection conduit can be one or more annular openings or a plurality of openings in an annular arrangement.

Figure 6:
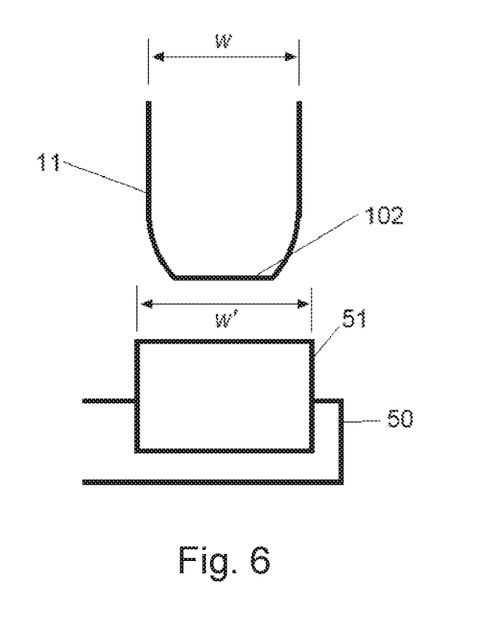
FIG. 6 shows an embodiment of a probe and well plate, in a state in which the probe is not collecting a sample.
Figure 7:
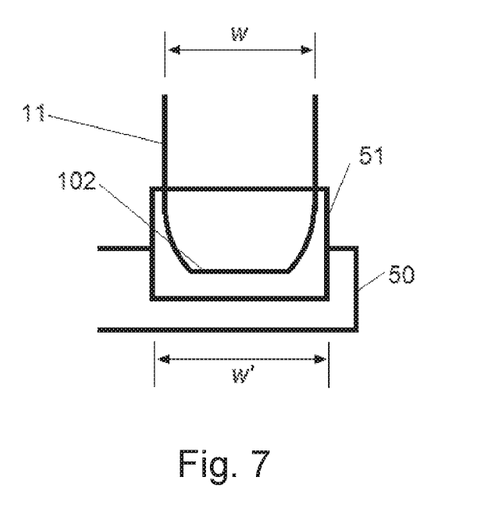
FIG. 7 shows an embodiment of a probe and well plate, in a state in which the probe is collecting a sample.

In some embodiments as shown in FIGS. 6 and 7, probe 11 may be configured for at least partial insertion into a sample container or plurality of sample containers, preferably a well 51 or a plurality of such wells in a well plate 50 or plurality of such well plates. In these embodiments, an outer width w of probe 11 is preferably less than an inner width w' of the well 51, thereby allowing for insertion of probe 11 into well 51. The outer width w of probe 11 may be the width of the probe 11 at open end 102 or, more preferably, may be the width of the probe 11 at an axial distance from open end 102 which is less than or approximately equal to the depth of well 51. In some embodiments, outer width w of probe 11 may be less than 7.0 mm, less than 5.0 mm, less than 3.3 mm, less than 1.7 mm, or less than 1.3 mm. In some embodiments, outer width w of probe 11 may be a width of the probe at the open end 102 of probe 11, or at an axial distance of from 5.0 to 25.0 mm from the open end 102 of probe 11, or at an axial distance of from 6.5 to 11.5 mm from the open end 102 of probe 11.

In other embodiments, probe 11 may not necessarily be configured for insertion into a sample container. For example some embodiments of probe 11 and/or analysis and/or sorting system 10 may be suitable for use with an apparatus for transmitting a sample from individual wells within a well plate to the open end 102 of probe 11, for example with an automated pipetting system, or by directing acoustic energy into the samples within individual wells to eject droplets of the sample. In these embodiments, the open end of the probe may point in an upward direction, a downward direction, a sideways direction, or at a skew angle with respect to a vertical direction. In some such embodiments, an upward direction for the probe and an inverted orientation of the sample container or containers may be particularly preferred. In still other embodiments, probe 11 may be configured to receive a sample or more preferably a plurality of samples without direct sampling from wells in a well plate, for example in the provision of drops or other small quantities of a sample or plurality of samples directly to the open end 102 of the probe 11.

In some embodiments, the analysis and/or sorting system 10 has only one probe 11 and no more. In other embodiments, analysis and/or sorting system 10 can comprise a plurality of probes. In cases where multiple probes 11 are utilized in parallel, the sampling rate may be multiplied accordingly, such as if autosampler 43 is configured to hold and/or move four probes simultaneously to collect samples and/or fluid from four different wells in parallel. In another embodiment, autosampler 43 may be configured to hold and/or move 2, 4, 6, 8, 16, 20, 24, 30, 48, 96, or more probes 11 in parallel.

In certain embodiments, a flow cytometer 20 can include a flow cell 21, a laser 22, and at least two containers 61a and 61b, which can be, for example, wells in a plurality of well plates or wells in the same well plate, as shown in FIGS. 1 and 2. Flow cytometer 20 is not particularly limited, except in that it is configured to sort components of a fluid stream from probe 11. In particular, flow cytometer 20 is configured to sort a sample into at least two containers 61a and 61b. A fluid stream provided to flow cytometer 20 can pass into flow cell 21, which can regulate the fluid stream such that many or most cells or other particles of the sample in the fluid stream emerge individually in separate droplets. In certain embodiments, the fluid stream thus regulated then passes through a measuring system. The measuring system can be, but is not limited to, an impedance, conductive, size exclusion, filtration, acoustic, thermodynamic, electromagnetic, mass spectrometric, or optical system. In some embodiments, the measuring system can include a laser beam emitted from laser 22, which can excite a fluorescent marker in a sample in the fluid stream. A detector can then detect the presence or absence of the fluorescent marker by the presence or absence of fluorescence. Some embodiments include more than one laser and/or more than one detector. In certain embodiments, droplets are charged, and droplets containing cells or particles marked with the fluorescent marker are sorted by their charges into one container 61a, while droplets containing cells or particles not marked with the fluorescent marker are sorted into a different container 61b, as shown in the embodiment in FIGS. 1 and 2. In other embodiments, droplet-based sorting is not used and instead, cells or particles marked with the fluorescent marker are sorted out of a fluid flow into one container 61a using a magnetic solenoid sorting valve, while unlabeled cells or particles are sorted into a different container. As further shown in FIGS. 1 and 2, these containers can be separate wells of a well plate, for example a microplate. In some configurations, flow cytometer 20 may sort samples into larger volume containers, tubes, cartridges or microchips.

In other embodiments, a flow cytometer may be configured for analysis of the sample and collection of data about the presence, content, frequency, and/or distribution of components within the sample having different properties, or satisfying various parameters. In particular, the flow cytometer may be configured to measure and collect data as to the presence and/or frequency of a labeled component, such as a labeled biological material, a labeled analysis reagent, or labeled particulate component. In some embodiments, flow cytometer 20 may be configured for both analysis and sorting, as both described above. In other embodiments, the flow cytometer may be configured for analysis alone without sorting, and the fluid stream comprising the sample may be discarded after analysis.

In still other embodiments, the flow cytometer 20 is a microfluidic sorting device configured for the sorting of samples into at least two containers 61a and 61b or other receiving points as directed by the microfluidic sorting device, for example, wells in a plurality of well plates or wells in the same well plate, as shown in FIGS. 1 and 2. The microfluidic sorting device is not particularly limited, except in that it is configured to sort components of a fluid stream from probe 11 based on any fluorescent, magnetic, isotopic, or chemical label or labels provided on the components, and/or based on a property or properties of the components unrelated to any label such as size, shape, density, binding capability, conductivity, or acoustic properties. A fluid stream provided to the microfluidic sorting device can be regulated by the microfluidic sorting device such that many or most cells or other particles of the sample in the fluid stream are separated into distinct components based on the labels and/or properties mentioned above. In certain embodiments, components containing a given set of labels and/or properties are separated and sorted into one container 61a, while components lacking the given set of labels and/or properties are sorted into a different container 61b, as shown in the embodiment in FIGS. 1 and 2. These containers can be separate wells of a well plate, for example a microplate. In some embodiments, for example in embodiments that do not involve analysis or sorting based on fluorescence or any other light- or radiation-based phenomenon, a microfluidic sorting device as flow cytometer 20 may not comprise a laser, in contrast with the embodiment of FIGS. 1 and 2, showing laser 22.

In some embodiments, for example as shown in FIGS. 1 and 2, analysis and/or sorting system 10 can include a probe input line 31, configured to supply a fluid to probe 11. Probe input line 31 is not particularly limited beyond its configuration for conveying a fluid stream to the probe 11. Probe input line 31 can be rigid, partially rigid, or flexible. Probe input line 31 is preferably a closed and sealed line to prevent introduction of air or gas into the fluid which it conveys. It can include a tube, hose, pipe, conduit through another element, or any combination thereof. It can be made of metal, glass, plastic, rubber, or any combination thereof, or any other material or combination of materials which can convey the fluid to the probe 11. Preferably, probe input line 31 comprises silicone or PVC tubing. In some embodiments, probe input line 31 can include or exclude valves, joints, and/or junctions. Preferably, probe input line 31 excludes any reciprocating valve. In some embodiments, probe input line 31 can include or exclude sample loops, preferably excluding sample loops. Probe input line 31 is joined to or integral with fluid supply 104 to provide fluid to fluid supply 104.

In some embodiments, for example as shown in FIGS. 1 and 2, probe input line 31 can include or be interrupted by a probe input pump 41, configured to supply a fluid to probe 11. Probe input pump 41 is not particularly limited, except in that it provides a fluid to probe 11. Probe input pump 41 can be any of various types of laboratory pumps including peristaltic pumps, diaphragm pumps, syringe pumps, gear pumps, or microfluidic pumps. Preferably, probe input pump 41 is a microfluidic pump. In other embodiments, a fluid can be conveyed through probe input line 31 to probe 11 in other ways. For example, a vacuum in or near probe 11 can reduce pressure at or near the end of probe input line 31, thereby causing the pressure (for example, ambient pressure) at a source of the fluid to push the fluid through probe input line 31. Force can also be applied to the fluid to convey it through probe input line 31, for example, by siphoning, or by gravity, from an elevated fluid source. The skilled artisan will understand that other methods of conveying fluid through a line are known and may be suitable for conveying the fluid to probe 11 through probe input line 31.

Analysis and/or sorting system 10 includes a probe to flow cytometer line 32. Probe to flow cytometer line 32 is not particularly limited beyond its configuration for conveying a fluid stream from the probe 11 to the flow cytometer 20. Probe to flow cytometer line 32 is joined to or integral with fluid exhaust 105 to provide fluid to fluid exhaust 105. Probe to flow cytometer line 32 can be rigid, partially rigid, or flexible. Probe to flow cytometer line 32 is preferably a closed and sealed line to prevent introduction of air or gas into the fluid stream which it conveys. It can include a tube, hose, pipe, conduit through another element, or any combination thereof. It can be made of metal, glass, plastic, rubber, or any combination thereof, or any other material or combination of materials which can convey the fluid stream to the flow cytometer 20. The material or materials of flow cytometer line 32 can be the same as or different from the materials of probe input line 31. Preferably, probe to flow cytometer line 32 comprises silicone or PVC tubing. In some embodiments, probe to flow cytometer line 32 can include or exclude valves, joints, and/or junctions. Preferably, probe to flow cytometer line 32 excludes any reciprocating valve. In some embodiments, probe to flow cytometer 32 can include or exclude sample loops, preferably excluding sample loops.

In some embodiments, for example as shown in FIGS. 1 and 2, probe to flow cytometer line 32 can include or be interrupted by a probe to flow cytometer pump 42, configured to draw a fluid stream from probe 11. Probe to flow cytometer pump 42 is not particularly limited, except in that it draws a fluid from probe 11 to provide it to flow cytometer 20. Probe to flow cytometer pump 42 can be any of various types of laboratory pumps including peristaltic pumps, diaphragm pumps, syringe pumps, gear pumps, or microfluidic pumps. Preferably, probe to flow cytometer pump 42 is a microfluidic pump. Probe to flow cytometer pump 42 can be the same type as or a different type from probe input pump 41. In other embodiments, a fluid can be conveyed through probe to flow cytometer line 32, from probe 11 to flow cytometer 20, in other ways. For example, a vacuum in or near flow cytometer 20 can reduce pressure at or near the end of probe to flow cytometer line 32, thereby causing the pressure (for example, ambient pressure) at the probe 11 to push the fluid through probe to flow cytometer line 32. Force can also be applied to the fluid to convey it through probe to flow cytometer line 32, for example, by siphoning or gravitational force from a difference in elevation between probe 11 and flow cytometer 20. The skilled artisan will understand that other methods of conveying fluid through a line are known and may be suitable for conveying the fluid from probe 11 to flow cytometer 20 through probe to flow cytometer line 32.

In some embodiments, for example as shown in FIGS. 1 and 2, analysis and/or sorting system 10 can further include a control system for controlling probe input pump 41 and probe to flow cytometer pump 42. The control system can monitor the flow through probe input line 31 and through probe to flow cytometer line 32 and can further monitor these two flows relative to one another. The control system can optionally include one or more flow meters for monitoring one or both of the flow through probe input line 31 and through probe to flow cytometer line 32. The control system can adjust the pumping power or other determinative parameters for probe input pump 41 and/or probe to flow cytometer 42, preferably both. The control system can include a graphical user interface. The control system can be integrated with or separate from a control system for flow cytometer 20.

In some embodiments, for example as shown in FIGS. 1 and 2, analysis and/or sorting system 10 can include an autosampler 43. In some embodiments, autosampler 43 comprises a holder for controllably holding and releasing probe 11, and for moving probe 11 between multiple sample containers and wells. In other embodiments, autosampler 43 is fixedly attached or integral with probe 11, and is configured to move probe 11 between multiple sample containers and/or wells. In still other embodiments, probe 11 may be configured to maintain a substantially fixed position during operation, while autosampler 43 comprises a holder for controllably holding and releasing a sample container, such as a sample holder, tube, and/or well plate, and for moving such a sample container to provide multiple samples for sampling by probe 11 in its fixed position. Autosampler 43 may be configured to collect separate samples from different wells or other containers at a rate of greater than 30 per minute, preferably at least 35 per minute, preferably at least 40 per minute, more preferably at least 45 per minute, even more preferably at least 60 per minute, and still further preferably at about 96 per minute. In some embodiments, autosampler 43 may be configured to collect separate samples from different wells or other containers at a rate of as high as 110 per minute or less. Embodiments involving these sample collection rates may particularly be embodiments in which probe 11 may be configured for at least partial insertion into a sample container or plurality of sample containers, preferably a well 51 or a plurality of such wells in a well plate 50 or plurality of such well plates.

The above-described system and substantially similar systems can be used in a method for selection and separation of different components within a sample.

A method of analyzing, sorting, separating, and/or selecting components in one or more samples can include conveying a fluid to an open end 102 of a probe 11, collecting at least one sample into the open end 102 of the probe 11, removing a fluid stream comprising the at least one sample and the fluid from the open end 102 of the probe 11, conveying the fluid stream to a flow cytometer 20, and analyzing and/or separating components of the sample with flow cytometer 20.

The sample is not particularly limited. In some embodiments, at least a portion of it may be labeled, preferably prior to collection with probe 11. In some preferred embodiments involving labeling, the sample comprises a labeled biological material or materials and also an unlabeled biological material or materials. The labeled and unlabeled biological material or materials may each independently comprise one or more cells, cell fragments, viruses, virus fragments, organelles, exosomes or extracellular vesicles and fragments thereof, proteins, nucleic acids, and/or carbohydrates. Proteins, if present, can include a protein complex, a multiprotein complex, a single polypeptide, an oligopeptide, or any combination thereof. Nucleic acids, if present, can include chromosomes, polynucleotides, oligonucleotides, a nucleic acid complex, or any combination thereof. Carbohydrates can include, for example, sugars, oligosaccharides, polysaccharides, a carbohydrate complex, or any combination thereof. The sample preferably comprises one or more cells, which in some embodiments may be immune cells, stem cells, or circulating tumor cells (CTCs). Examples of immune cells that may be included in the sample include leukocytes such as T cells, B cells, natural killer (NK) cells, dendritic cells, monocytes, and macrophages. Native or engineered T cells are preferred as leukocytes in certain embodiments, and may include tumor infiltrating lymphocytes, T cells including one or more chimeric antigen receptor proteins, or T cells including one or more T cell receptor proteins suitable for the diagnosis or treatment of cancer, infectious diseases, or autoimmune diseases. In other embodiments, the leukocytes may include native or engineered B cells, in particular engineered B cells suitable for the diagnosis or treatment of cancer, autoimmune diseases, infectious diseases, or protein deficiency diseases. In still other embodiments, the leukocytes may be native or engineered NK cells, for example NK cells including a chimeric antigen receptor protein, in particular those suitable for treatment of cancer, infectious diseases, or autoimmune diseases. In further embodiments, the leukocytes may be native or engineered dendritic cells, for example engineered dendritic cells suitable for the diagnosis or treatment of cancer, infectious diseases, inflammatory diseases, degenerative diseases, autoimmune diseases, and organ transplantation. In still further embodiments, the leukocytes may be native or engineered monocytes, for example engineered monocytes suitable for the diagnosis or treatment of cancer, infectious diseases, inflammatory diseases, degenerative diseases, autoimmune diseases, and organ transplantation. In other embodiments, the leukocytes may be native or engineered macrophages, for example engineered macrophages suitable for the diagnosis or treatment of cancer, infectious diseases, inflammatory diseases, degenerative diseases, autoimmune diseases, and organ transplantation. Stem cells may include, for example, embryonic stem cells, neural stem cells, mesenchymal stem cells, hematopoietic stem cells, or induced pluripotent stem cells (iPSCs). Embodiments with a sample comprising stem cells may include stem cells suitable for genetically engineered correction of a disease or condition, or for transplantation. The stem cells, if present, may be suitable for the treatment of neurodegeneration, diabetes, multiple sclerosis, cerebral palsy, macular degeneration, cardiovascular diseases, or musculoskeletal diseases. CTCs may include, without limitation, tumor cells released from a solid or primary tumor into the surrounding vasculature or lymphatic system to then circulate in the bloodstream. CTCs may be suitable for the detection and diagnosis of cancer. Where the sample includes cells, the cells may be bacterial cells, plant cells, yeast or fungal cells, or animal cells. In certain embodiments, the cells are preferably engineered or native animal cells, and in particular embodiments, the cells are more preferably engineered or native human cells. The labeled and unlabeled biological material or materials may be naturally-occurring, or may be modified from their native states for example by mutation or genetic engineering, or may be a combination of both types of materials. In some preferred embodiments, the sample includes at least one modified and labeled biological material, preferably including one or more modified and labeled cells.

In some preferred embodiments, the sample has been originally or initially obtained from a subject. The subject may be a human subject, another organism, or a tissue sample, preferably a human subject or a human tissue sample. The subject may preferably be a patient in need of treatment, or in other embodiments, the subject is a different individual from a patient in need of treatment. The sample may be initially obtained from the subject as a blood sample or as a tissue sample, preferably as a blood sample and/or a sample obtained from a tumor, particularly a tumor stroma, or other tissue subject to a condition in need of treatment. After the sample is initially obtained from the subject, at least one component of the blood and/or tissue may be removed or isolated as the sample. The component to be removed or isolated as the sample may comprise one or more cells, cell fragments, viruses, virus fragments, exosomes or extracellular vesicles and fragments thereof, proteins, nucleic acids, or carbohydrates. The component to be removed or isolated as the sample is preferably one or more cells, more preferably leukocytes, and in particular, T cells are preferred in certain embodiments.

In preferred embodiments, once the sample has been removed or isolated, it is modified, or it is used to modify another biological material. Modification may include genetic engineering, including the introduction of DNA and/or RNA into a cell, in order to express a desired trait and/or produce a desired structure, preferably a protein; alternatively, the modifications may have the goal of removing or inhibiting the expression of a desired trait and/or production of a desired structure. In certain preferred embodiments, the removed or isolated sample comprises T cells, and the modification comprises providing the T cells with DNA which encodes for one or more receptor proteins. In these embodiments, the receptor protein can be a T cell receptor or chimeric antigen receptor configured to selectively bind to one or more tumor cell antigens. In some embodiments, the receptor protein is an anti-CD19 chimeric antigen receptor.

In some embodiments related to tumor-infiltrating lymphocyte (TIL) adoptive cell therapy, the sample may be initially obtained from blood or a tumor from a patient in need of treatment. The sample may be sorted to separate TILs, such as T cells, and tumor cells. In some embodiments, separated T cells may be further isolated as individual single cells. T cells are expanded ex vivo and then exposed to the tumor cells to identify T cells that react against the tumor cells. In some embodiments, the reactive T cells may be identified and selected for reactivity by the presence of cell surface proteins, such as but not limited to CD137/4-1BB, CD134/OX40, and/or CD107a/LAMP-1. T cells that indicate as reactive to the tumor cells may be selected and further expanded to be infused back into the patient with IL-2 treatment to promote expansion and engraftment.

In other embodiments, the sample includes reagents or particulate components, which may be suitable for sorting or analysis, or for facilitating a sorting or analysis method. Reagents or particulate components can include beads. Such reagents or particulate components may be present in the sample instead of, or in addition to, a biological material. In some embodiments, the reagents or particulate components are provided with one or more biological materials. For example, a surface of a bead may be provided with an antibody, in particular an antibody configured to capture cells or other biological materials. The reagents or particulate components, for example beads, may include a label, for example a fluorescent or magnetic label. Such a label may be provided within the bead and/or on a surface of the bead, either directly or via a linking group.

To facilitate analysis, separation, selection, and/or sorting, the biological material may be labeled, preferably in a selective manner, and preferably prior to collection with probe 11. The label may be a chemical, isotopic, magnetic, or fluorescent type label. In some embodiments, the label preferably includes a label which is suitable for detection in an optical manner, in particular a fluorescent label, for example phycoerythrin (PE) or carboxyfluorescein succinimidyl ester (CFSE), or fluorescent proteins such as enhanced GFP (eGFP), or nanoparticles such as quantum dots. The label can also include a magnetic label, instead of an optical label, or in some preferable embodiments in addition to an optical label. If the labeling is selective, then the selective labeling may be selective for the presence of a target biological material, such as a for a protein or receptor marker on the surface of a cell in the sample, for example a T cell receptor or chimeric antigen receptor capable of binding to one or more tumor cell antigens, such as an anti-CD19 chimeric antigen receptor. In other embodiments, the labeling may be selective for the presence of surface protein markers that indicate an activated or reactive T cell, for example, CD137/4-1BB, CD134/OX40, and/or CD107a/LAMP-1. A label may include one or more labels for different characteristics and/or markers, such as for the presence of different proteins, or for the presence of a protein and another characteristic. In such a plurality of labels, the labels may be the same or different.

To obtain the sample in the open end 102 of the probe 11, a fluid may be provided from fluid supply 104. The fluid is preferably a liquid, more preferably a saline solution, even more preferably a buffered saline solution. The buffer, if present, may be a phosphate buffer. In some embodiments, the fluid is a fluid suitable as a sheath fluid for flow cytometry, or a fluid which can be combined with one or more other substances to provide a sheath fluid for flow cytometry. Preferably, the fluid itself as provided through fluid supply 104 to open end 102 is suitable as a sheath fluid for flow cytometry.

The fluid may be provided to fluid supply 104 by pumping, for example with a probe input pump 41. In preferred embodiments, the flow rate of the fluid through fluid supply 104 to open end 102 is regulated, which may include measuring with a flow meter and/or regulating the flow rate with a flow regulator. The flow rate of the fluid through fluid supply 104 to open end 102 is, in some embodiments, also a volumetric flow rate suitable for flow cytometry. In such embodiments, the flow rate may be from 10 to 1,000 μL/min, in particular from 10 to 20 μL/min or from 100 to 1,000 μL/min. The flow rate of the fluid through fluid supply 104 to open end 102 may be greater than, substantially the same as, or identical to a flow rate for removing a fluid stream from the open end 102 of probe 11 through the fluid exhaust 105. In some embodiments, the flow rate of the fluid through fluid supply 104 to open end 102 is from 1% to 10% greater than a flow rate for removing a fluid stream from the open end 102 of probe 11 through the fluid exhaust 105, more preferably about 5% greater. By maintaining a sufficient flow rate through fluid supply 104 to open end 102 so as to replace at least the fluid removed through fluid exhaust 105, the probe 11 in the analysis and/or sorting system 10 and the method of using it can avoid intake of air or other gas into fluid exhaust 105, thereby avoiding the undesired presence of gas into a flow cytometer 20.

Upon arrival at open end 102 of probe 11, the fluid may form a fluid dome 107 as shown in FIG. 5. A sample may enter open end 102 by contact with fluid dome 107. In some embodiments, the sample may enter the fluid dome 107 when the fluid dome 107 contacts a sample, for example a sample as such or an aqueous suspension or dispersion of the sample, in a sample container or containers such as tubes, flasks, or a well 51 of a well plate 50. In other embodiments, the sample could be provided to open end 102, preferably having dome 107, by provision of drops or sprays of the sample to open end 102. For example, some embodiments of the method may convey sample to open end 102 of probe 11 with an automated pipetting system, or by directing acoustic energy into the samples within individual wells to eject droplets of the sample toward open end 102 of probe 11. In some such embodiments, for example where the wells or other sample container or containers are sufficiently narrow so as to retain the sample by forces such as surface tension or adhesion even in other orientations, the open end of the probe may point in an upward direction, a downwards direction, a sideways direction, or at a skew angle with respect to a vertical direction. In some such embodiments, an upward direction for the probe and an inverted orientation of the sample container or containers may be particularly preferred. In some cases, sample and/or fluid may be drawn into the probe without formation of a dome.

A fluid stream comprising the fluid and the sample may be removed from open end 102 through fluid exhaust 105 by pumping, for example with a probe to flow cytometer pump 42. In preferred embodiments, the flow rate of the fluid stream through fluid exhaust 105 out from open end 102 is regulated, which may include measuring with a flow meter and/or regulating the flow rate with a flow regulator. In addition or in the alternative, a sensor may be used to directly or indirectly measure the flow rate. For example, a sensor, such as a light-based sensor, may measure the size and/or shape of dome 107 in order to maintain a balance between the flow rate through fluid supply 104 and the flow rate through fluid exhaust 105. In some embodiments, a processor may be used to monitor and/or control the flow rate through fluid supply 104 and the flow rate through fluid exhaust 105. Such a processor, if present, may receive data from one or more flow meters and/or one or more sensors such as light-based sensors. Additionally or alternatively, such a processor, if present, may provide data to control one or more flow regulators. The flow rate of the fluid stream through fluid exhaust 105 away from open end 102 is, in some embodiments, also a volumetric flow rate suitable for flow cytometry. In such embodiments, the flow rate may be from 10 to 1,000 µL/min, in particular from 10 to 20 µL/min or from 100 to 1,000 L/min. The flow rate of the fluid stream through fluid exhaust 105 out from open end 102 may be less than, substantially the same as, or identical to a flow rate of the fluid through fluid supply 104 to open end 102. In some embodiments, the flow rate through fluid exhaust 105 out from open end 102 is from 1% to 10% less than a flow rate through fluid supply 104 to open end 102, more preferably about 5% less. By maintaining a sufficiently low flow rate through fluid exhaust 105 so as to prevent intake of gas or air along with the sample and the fluid supplied through fluid supply 104 to open end 102, the probe 11 in the analysis and/or sorting system 10 and the method of using it can avoid the undesired presence of gas into a flow cytometer 20.

The fluid stream removed from open end 102 of the probe 11 through fluid exhaust 105 of the probe 11 is then conveyed to the flow cytometer 20. In some embodiments, probe to flow cytometer line 32 transports the fluid stream. Probe to flow cytometer line 32 can be free of joints, junctures, or valves in some embodiments; in other embodiments, probe to flow cytometer line 32 includes at least a joint, juncture, or valve. The implementation of probe 11 to avoid the undesired presence of gas in the fluid stream may mean that, in some embodiments, the presence of a joint, juncture, or valve may cause fewer problems, as no air or gas bubbles would be provided into probe to flow cytometer line 32 to be retained deleteriously in the joint, juncture, or valve, thereby disrupting the flow of the fluid stream through probe to flow cytometer line 32.

As the fluid stream is conveyed from open end 102 of the probe 11 through fluid exhaust 105 of the probe 11 to the flow cytometer 20, the fluid stream may or may not receive or be joined by an additional component or components. In some embodiments, the fluid stream travels without added components to the flow cytometer 20. In other embodiments, the fluid stream may be diluted with water, or an optionally-buffered saline solution may be added.

Once in the flow cytometer 20, the fluid stream may in some embodiments be separated, for example though fluorescence-activated cell sorting. In some embodiments, the separation process includes regulation of flow of the fluid stream, preferably by hydrodynamic focusing, including generation of a sheath flow with the fluid stream comprising the sample in a middle portion thereof. In other preferred embodiments, the fluid flow can be regulated by acoustic focusing with ultrasonic waves to enhance generation of a sheath flow with the fluid stream including the sample in a middle portion thereof. The fluid stream can then be separated into droplets, most or all of which preferably contain one cell or other unit of the biological material, and the droplets may each be provided with a charge. A label, when present in a droplet, is then detected. Detection in some embodiments includes provision of electromagnetic energy, preferably in the form of a laser beam, to the droplets. The energy may then excite the label, preferably through fluorescent excitation. A camera or other light-detecting apparatus can then detect the presence or absence of fluorescence, thereby detecting the presence or absence of a labeled sample in the droplet. Droplets of the fluid stream can then be sorted based on the detected presence or absence of the labeled sample, including directing of the droplets to at least two containers or other receiving points such as wells in a well plate, tubes, or flasks through the charge provided to the droplets. In other embodiments, labeled sample is sorted out of a fluid flow using a magnetic solenoid sorting valve into at least two containers based on the detected presence or absence of the label. By these or other methods of flow cytometry-based sorting, the sample can be separated into at least one labeled component and at least one unlabeled or differently-labeled component. In certain embodiments, labeled components may be sorted as single or individual components into individual containers. For example if the labeled components are cells single or individual cells may be sorted into individual containers as the only labeled component within that container.

In still other embodiments, sorting by flow cytometry may comprise sorting the sample by microfluidic sorting into at least two containers 61a and 61b or other receiving points as directed by the microfluidic sorting device, for example, wells in a plurality of well plates or wells in the same well plate, as shown in FIGS. 1 and 2. Microfluidic sorting is not particularly limited, except in that it sorts components of a fluid stream from probe 11 based on any fluorescent, magnetic, isotopic, or chemical label or labels provided on the components, and/or based on a property or properties of the components unrelated to any label such as size, shape, density, binding capability, conductivity, or acoustic properties. Microfluidic sorting may involve regulating the fluid stream such that many or most cells or other particles of the sample in the fluid stream are separated into distinct components based on the labels and/or properties mentioned above. In certain embodiments, components containing a given set of labels and/or properties are separated and sorted into one container 61a, while components lacking the given set of labels and/or properties are sorted into a different container 61b, as shown in the embodiment in FIGS. 1 and 2. These containers can be separate wells of a well plate, for example a microplate, or separate tubes. In some embodiments, for example in embodiments that do not involve analysis or sorting based on fluorescence or any other light- or radiation-based phenomenon, a microfluidic sorting device as flow cytometer 20 may not comprise a laser, in contrast with the embodiment of FIGS. 1 and 2, showing laser 22.

In some embodiments, after sorting by flow cytometry, one or more resultant fluid streams, fractions, and/or containers comprising sorted components may be enriched for labeled components of the sample, meaning labeled components are present in a greater number and/or amount relative to other fractions collected (e.g., the one or more second fluid streams, fractions, and/or containers). In some cases, being enriched for labeled components may refer to a measurable or detectable number or amount of labeled components. For example, an enriched fraction may contain at least 90, 91, 93, 95, 96, 97, 98, 99, 99.5, 99.8%, or more of the labeled components relative to unlabeled components in the fraction, or relative to the amount of total labeled components within the original sample. In some configurations, the unlabeled components may be collected in one or more second fractions. These may be discarded or analyzed. The one or more second fractions containing the unlabeled components are substantially devoid or depleted of labeled components. For example, these fractions may contain less than 15%, 10%, 5%, 4%, 3%, 2%, 1%, or none of the labeled component relative to the fractions enriched for labeled components. In some cases, this relative amount may be based upon a particle count, an amount by mass, a weight %, target label intensity, etc. A determination of amount may be made using techniques well known in the art such as by absorption, mass spectrometry, a chromatograph, a cell counter, an enzymatic assay (e.g., a horseradish peroxidase-based assay, ELISA), a colorimetric assay, a fluorescent assay, or the like.

In some embodiments, after separation in the flow cytometer 20, one or more components obtained from the sample may be prepared for administration to a subject in need of treatment. In some embodiments, where the one or more components obtained from the sample comprise cells, the cells may be cultivated. In addition, pharmaceutical adjuvants may be added, and certain components including the label may be removed, if desired.

In some embodiments, after separation in the flow cytometer 20 and in some embodiments after further preparation, one or more components obtained from the sample may be administered to a patient in need of treatment. The patient may be in need of treatment, for example, for cancer, in particular melanoma, acute lymphocytic leukemia, ovarian cancer, colon cancer, prostate cancer, brain cancer, or breast cancer.

The system and method may be further useful with respect to cell-based therapies, including other aspects of T cell receptor (TCR) therapy, chimeric antibody receptor T cell (CAR-T) therapy, tumor-infiltrating lymphocyte (TIL) therapy, or any combination thereof, for example as discussed in Ping, Y. et al., "T-cell receptor-engineered T cells for cancer treatment: current status and future directions" *Protein Cell* 2018 9(3):254-256, the entirety of which is incorporated herein by reference.

In other embodiments, the sample may be analyzed in the flow cytometer and data may be collected about the presence, content, frequency, and/or distribution of components within the sample having different properties, or satisfying various parameters. In particular, the sample may be measured and data may be collected as to the presence and/or frequency of a labeled component, such as a labeled biological material, a labeled analysis reagent, or labeled particulate component. In some embodiments, analysis by flow cytometry may be combined with sorting by flow cytometry, as both described above. In other embodiments, analysis by flow cytometry may occur without sorting, and the fluid stream comprising the sample may be discarded after analysis.

Any reference in this specification to an "embodiment" means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments. The features of any one embodiment may be combined with features of one or more other embodiments described herein to form additional embodiments.

Although the present invention has been described herein with reference to a number of illustrative embodiments, one skilled in the art could devise numerous other modifications and embodiments that will fall within the spirit and scope of the principles of this invention. More particularly, reasonable variations and modifications are possible in the component parts and/or arrangements of the subject combination arrangement within the scope of the foregoing disclosure, the drawings and the appended claims without departing from the spirit of the invention. In addition to variations and modifications in the component parts and/or arrangements, alternative uses will also be apparent to those skilled in the art.

I claim:

1. An analysis and/or sorting method, comprising:
conveying a first fluid within a probe to an open end of the probe,
collecting at least one sample, comprising at least one first component and at least one second component, into the open end of a probe,
removing a fluid stream comprising the at least one sample and the first fluid from the open end of the probe,
conveying the fluid stream to a flow cytometer, and
analyzing the fluid stream by flow cytometry, and/or separating the fluid stream into at least a first separated stream comprising the at least one first component and a second separated stream comprising the at least one second component by flow cytometry,
wherein the fluid stream is substantially free of air bubbles when the fluid stream is conveyed to the flow cytometer, and wherein the fluid stream is substantially free of a gas/liquid interface when the fluid stream is conveyed to the flow cytometer.

2. The method of claim 1, wherein the at least one sample comprises a first sample, initially contained in a first container, and a second sample, initially contained in a second container.

3. The method of claim 2, wherein the first container is a first well in a plate and the second container is a second well in the same plate.

4. The method of claim 2, wherein the first container is a well in a first plate and the second container is a well in a second plate.

5. The method of claim 1, wherein the at least one sample comprises a plurality of samples, and wherein samples are collected at a rate of greater than 30 samples per minute.

6. The method of claim 1, wherein the first fluid is water or a sheath fluid or other fluid medium suitable for flow cytometry.

7. The method of claim 1, wherein the first fluid is a buffered aqueous saline solution or a cell culture medium.

8. The method of claim 7, wherein the first fluid is a buffered aqueous saline solution comprising a phosphate buffer.

9. The method of claim 1, wherein the at least one sample comprises cells.

10. The method of claim 1, wherein at least a portion of the sample is labeled with a fluorescent label, a magnetic label, an isotopic label, a chemical label, or any combination thereof.

11. The method of claim 10, wherein the at least one first component comprises a labeled component and wherein the at least one second component comprises a component which is not labeled.

12. The method of claim 1, wherein the at least one sample comprises leukocytes, stem cells, or circulating tumor cells.

13. The method of claim 1, wherein the at least one sample comprises T cells.

14. The method of claim 13, wherein at least some of the T cells comprise a T cell receptor or a chimeric antigen receptor.

15. The method of claim 1, wherein the at least one sample comprises tumor infiltrating lymphocytes.

16. The method of claim 1, wherein the at least one first component comprises T cells comprising a T cell receptor or a chimeric antigen receptor and wherein the at least one second component comprises cells which are substantially free of T cell receptors and chimeric antigen receptors.

17. The method of claim 1,
wherein the conveying the first fluid to the open end of the probe comprises pumping the first fluid with a first pump, and
wherein removing the fluid stream from the open end of the probe comprises removing the fluid stream with a second pump.

18. The method of claim 17, further comprising:
controlling a first flow rate of the first fluid into the open end of the probe, and simultaneously
controlling a second flow rate of the fluid stream from the open end of the probe.

19. The method of claim 1, further comprising:
adding a second fluid to the fluid stream, before, during, or after conveying the fluid stream to the flow cytometer,
wherein the second fluid is the same as or different from the first fluid.

20. An analysis and/or sorting method, comprising
conveying a first fluid within a probe to an open end of the probe,
collecting at least one sample from at least one sample container, the sample comprising at least one first component and at least one second component, into the open end of a probe,
removing a fluid stream, substantially free of air bubbles, and comprising the at least one sample and the first fluid, from the open end of the probe,
conveying the fluid stream to a flow cytometer, and
analyzing the fluid stream by flow cytometry, and/or separating the fluid stream into at least a first separated stream comprising the at least one first component and a second separated stream comprising the at least one second component by flow cytometry,
wherein the fluid stream is substantially free of air bubbles when the fluid stream is conveyed to the flow cytometer, wherein the fluid stream is substantially free of a gas/liquid interface when the fluid stream is conveyed to the flow cytometer, and wherein the at least one sample container is not moved when collecting the at least one sample.

* * * * *